US007008221B2

(12) United States Patent
McGann

(10) Patent No.: US 7,008,221 B2
(45) Date of Patent: Mar. 7, 2006

(54) SYSTEM FOR AUTOMATIC SELECTION OF AN ARCHWIRE

(75) Inventor: Benson D. McGann, San Juan Capistrano, CA (US)

(73) Assignee: Progressive America, Inc., Santa Ana, CA (US)

(*) Notice: Subject to any disclaimer, the term of this patent is extended or adjusted under 35 U.S.C. 154(b) by 30 days.

(21) Appl. No.: 10/695,084

(22) Filed: Oct. 27, 2003

(65) Prior Publication Data
US 2004/0086827 A1 May 6, 2004

Related U.S. Application Data

(62) Division of application No. 10/131,454, filed on Apr. 22, 2002, now Pat. No. 6,679,700.

(60) Provisional application No. 60/350,233, filed on Jan. 16, 2002.

(51) Int. Cl.
*A61C 3/00* (2006.01)
(52) U.S. Cl. .................................................... 433/24
(58) Field of Classification Search .............. 433/24, 433/20, 3, 215; 705/26
See application file for complete search history.

(56) References Cited

U.S. PATENT DOCUMENTS 5,533,895 A * 7/1996 Andreiko et al. ............. 433/24
6,089,868 A * 7/2000 Jordan et al. ............... 433/215
6,315,553 B1 * 11/2001 Sachdeva et al. ............. 433/24
6,350,120 B1 * 2/2002 Sachdeva et al. ............. 433/24
6,582,225 B1 * 6/2003 Bergersen ....................... 433/2
6,688,885 B1 * 2/2004 Sachdeva et al. ............. 433/24
6,736,638 B1 * 5/2004 Sachdeva et al. ............. 433/24

* cited by examiner

*Primary Examiner*—Todd E. Manahan
(74) *Attorney, Agent, or Firm*—Snell & Wilmer L.L.P.; David J. Zoetewey

(57) ABSTRACT

The present invention is directed to selection of individual patient archwires by examining the patients inner arch rather than the patients teeth. In particular, a method of archwire selection comprises (a) obtaining a representation of a patient's inner arch curve (a "PIAC"); (b) selecting an archwire shape based at least partially on the PIAC representation; (c) making an initial selection of an archwire size based at least partially on the PIAC representation; (d) selecting a final archwire size after considering something other than the PIAC representation; and (e) selecting an archwire to be used based on the selected archwire shape and selected final archwire size. Using the PIAC rather than the occlusal or labial and buccal surfaces of the teeth for archwire shape selection promotes shaping the teeth to the shape of the jaw bone and gives consistent facial esthetics plus better retention of the treatment correction. Use of a patients PIAC/jaw bone structure also facilitates automating the process of archwire selection.

12 Claims, 9 Drawing Sheets

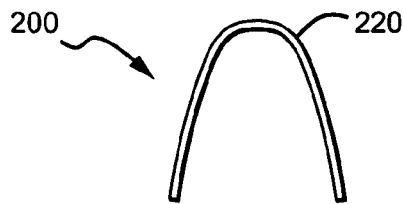
FIG. 5
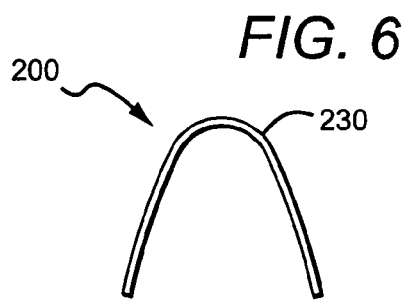
FIG. 6
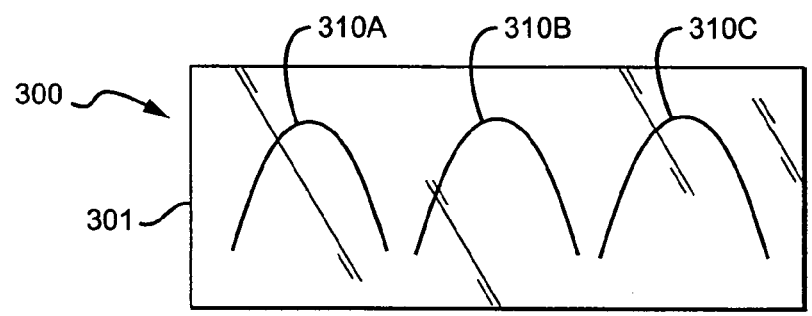
FIG. 7
FIG. 8
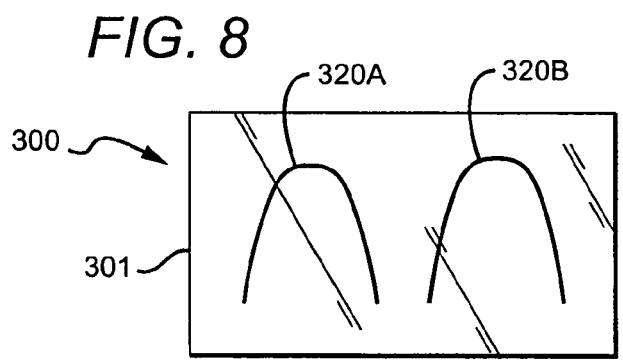
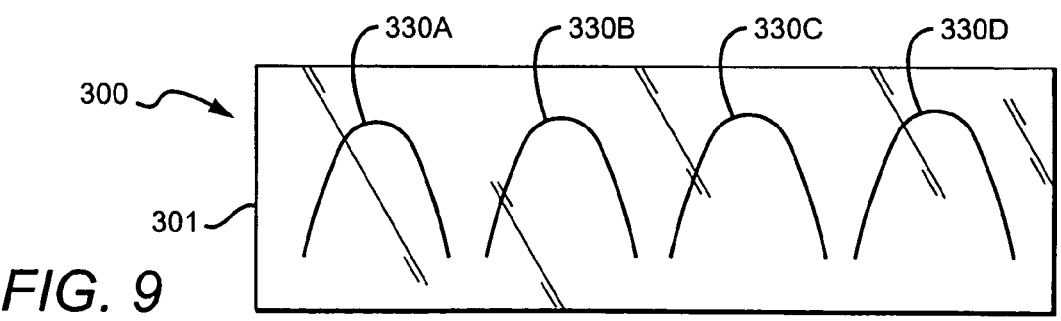
FIG. 9

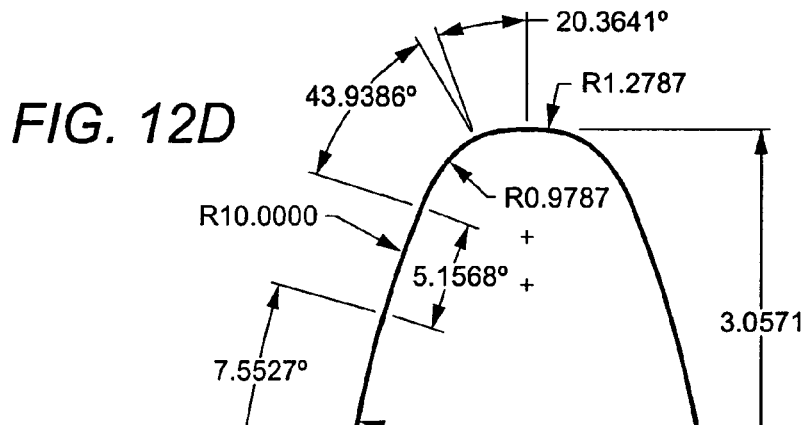
FIG. 12D
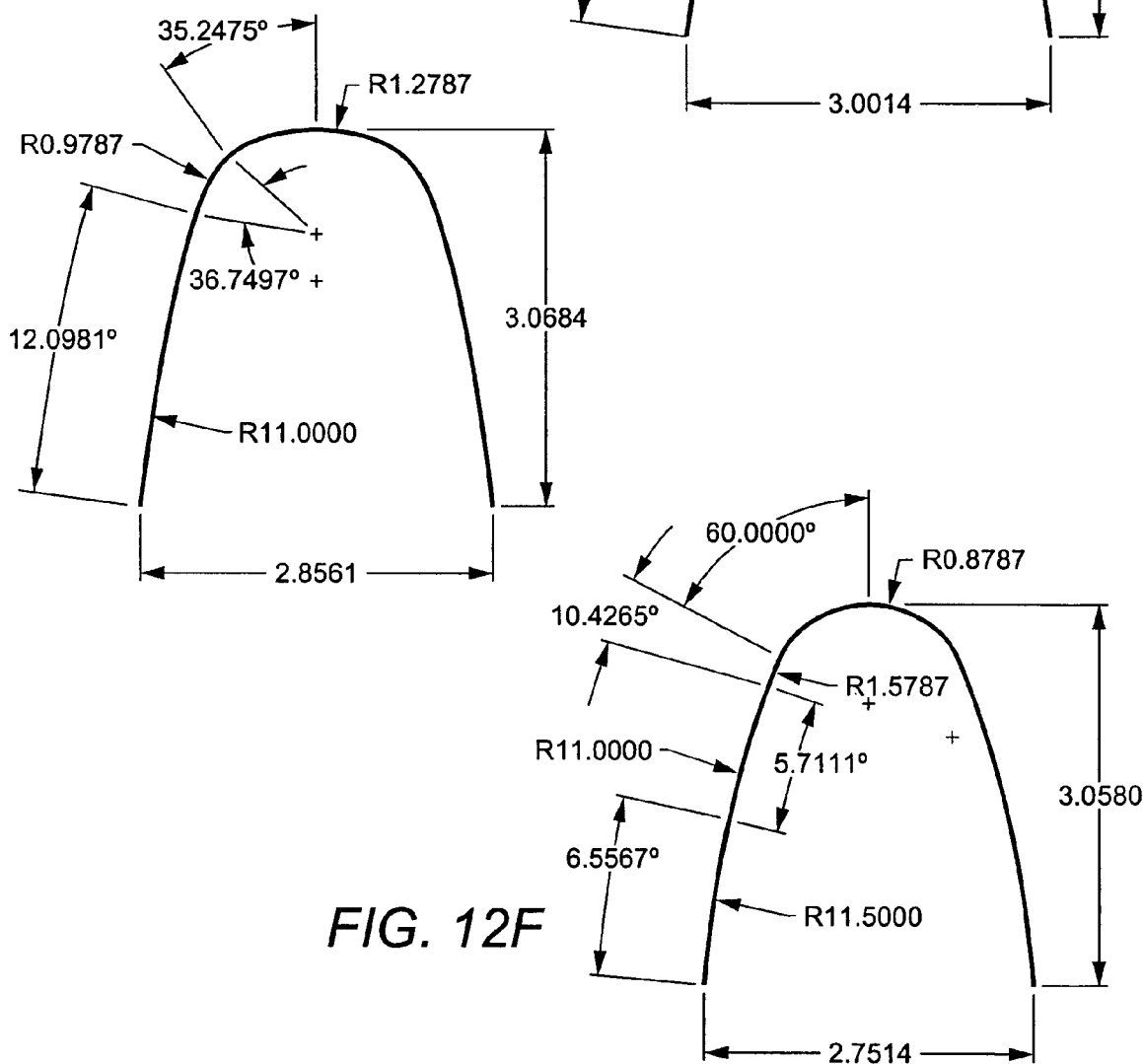
FIG. 12E
FIG. 12F

SYSTEM FOR AUTOMATIC SELECTION OF AN ARCHWIRE

This application is a divisional of application Ser. No. 10/131,454, filed Apr. 22, 2002, which issued as Pat. No. 6,679,700 which claims benefit of Provisional Application No. 60/350,233, filed Jan. 16, 2002.

This application claims the benefit of U.S. provisional application No. 60/350,233 incorporated herein by reference in its entirety.

FIELD OF THE INVENTION

The field of the invention is orthodontics.

BACKGROUND OF THE INVENTION

Dentists, orthodontists in particular, often use orthodontic hardware such as brackets and archwires in the prevention or correction of irregularities of the teeth. An orthodontic bracket is generally a metal or ceramic part fastened to a tooth to serve as a means for fastening an archwire. An archwire is a metal wire that is attached to the brackets to move the teeth of a patient in a manner desired by the patient's dentist. In treating a patient, a dentist will generally use a standard set of 24–28 brackets and 1 archwire engaged into these brackets to apply the forces needed for tooth movement.

Archwires generally vary in regard to shape, size, and type of wire used. In previously known methods, initial selection of an archwire is typically accomplished by examination of a patient's teeth to determine what size and shape of archwire would be appropriate for that patient. In many instances, the shape to be used is determined by looking at the shape formed by the occlusal surfaces of the teeth, or by looking at the shape formed by the labial and buccal surfaces of the teeth. Unfortunately, determining an appropriate shape by looking at the occlusal or the labial and buccal surfaces of a patient's teeth does not always result in selection of the optimum archwire shape. Such selection is generally made more difficult due to variations in tooth shape, position and orientation. Moreover, although taught in school, selecting custom archwire shapes for each individual patient is generally too time consuming for the dentist/orthodontist, reducing the number of patients that can be seen in a day, and increasing the fee for those patients being treated.

SUMMARY OF THE INVENTION

The present invention is directed to selection of individual patient archwires by examining the patients inner arch rather than the patients teeth. In particular, a preferred method of archwire selection comprises (a) obtaining a representation of a patient's inner arch curve (a "PIAC"); (b) selecting an archwire shape based at least partially on the PIAC representation; (c) making an initial selection of an archwire size based at least partially on the PIAC representation; (d) selecting a final archwire size after considering something other than the PIAC representation; and (e) selecting an archwire to be used based on the selected archwire shape and selected final archwire size. Using the PIAC rather than the occlusal or labial and buccal surfaces of the teeth for archwire shape selection promotes shaping the teeth to the shape of the jaw bone, and gives consistent facial esthetics plus better retention of the treatment correction.

It is contemplated that such a method of archwire selection may advantageously be at least partially used as part of an automated system for selecting an archwire for a patient comprising: a patient internal arch curve recorder adapted to obtain a representation of the patient's internal arch curve; data on available archwires; and a mechanism adapted to compare an obtained representation of a patient's internal arch curve with the data on available archwires and to identify an archwire based on any such comparison. Similarly, it may advantageously be used, at least in part, in a system for selecting and ordering an archwire for a patient comprising means for selecting an archwire from a plurality of available archwires; and means for ordering the selected archwire from an archwire supplier; wherein the selection of an archwire is based, at least in part, on all of the following factors: the patient's jawbone structure; a dentists preferred treatment option; and the sizes and shapes of available archwires.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

FIG. 5 is a top view of a square archwire.

FIG. 6 is a top view of an ovoid archwire.

FIG. 7 is a top view of a translucent sheet bearing representations of various different sized tapered archwires.

FIG. 8 is a top view of a translucent sheet bearing representations of various different sized square archwires.

FIG. 9 is a top view of a translucent sheet bearing representations of various different sized ovoid archwires.

FIG. 12D is a dimensioned view of a medium, square, upper archwire.

FIG. 12E is a dimensioned view of a large, square, upper archwire.

FIG. 12F is a dimensioned view of a small, ovoid, upper archwire.

DETAILED DESCRIPTION

Figure 1:
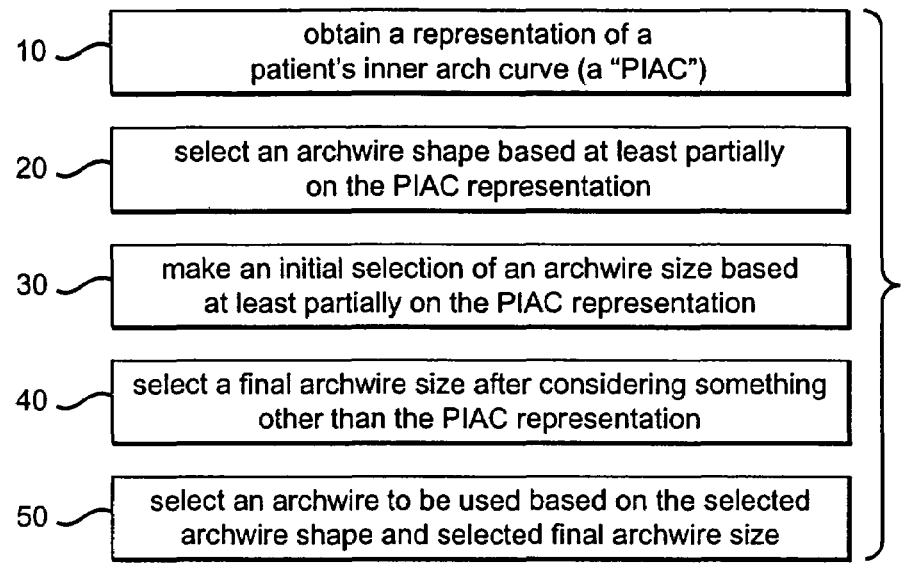
FIG. 1 is diagram of a first method of archwire selection.

Referring to FIG. 1, a method of archwire selection comprises: step 10, obtaining a representation of a patient's inner arch curve (a "PIAC"); step 20, selecting an archwire shape based at least partially on the PIAC representation; step 30, making an initial selection of an archwire size based at least partially on the PIAC representation; step 40 selecting a final archwire size after considering something other than the PIAC representation; and step 50, selecting an archwire to be used based on the selected archwire shape and selected final archwire size. Using the PIAC rather than the occlusal or labial and buccal surfaces of the teeth for archwire shape selection promotes shaping the teeth to the shape of the jaw bone and gives consistent facial esthetics plus better retention of the treatment correction.

A PIAC, as the term is used herein, is the curve formed by the jaw-bone structure of the patient. It is contemplated that the PIAC is best represented by the curve formed where the surface formed by the patient's gums transitions from the surface formed by the portion of the gums covering the patient's upper or lower arch to the surface formed by the portion of the patient's gums covering the bases of the interior surfaces of the patient's teeth. As a patient has upper and lower arches, the PIAC corresponding to the upper arch will be referred to as the "upper PIAC", and the PIAC corresponding to the lower arch will be referred to as the "lower PIAC". In instances herein where what is being discussed can be applied to either or both the upper PIAC and lower PIAC, the acronym "PIAC" will not be preceded by either the word upper or lower. A similar convention will be followed in regard to the term "arch" as well. The PIAC will typically be visible if one views an image or study model of the patient's teeth and arch.

Figure 2:
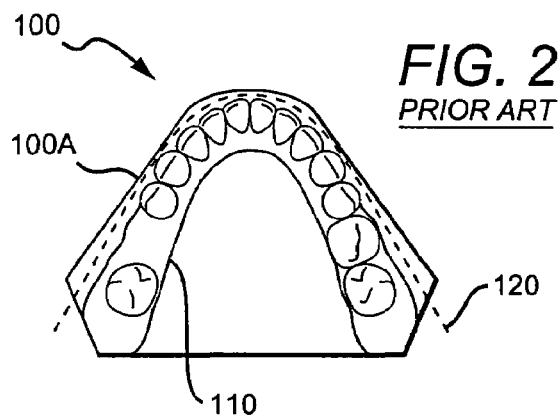
FIG. 2 is a top view of a patient's study model.
Figure 3:
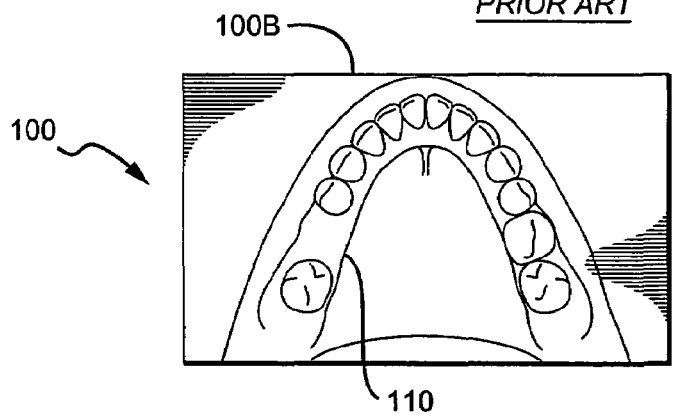
FIG. 3 is a top view of an image of a patient's teeth and arch.

Referring to FIGS. 2 and 3, obtaining a representation 110 of the PIAC may be accomplished in a number of ways including but not necessarily limited to obtaining a study model 100A of the patient's teeth and arch, obtaining an image 100B of the patient's teeth and arch, and obtaining an electronic representation (not shown) of the patient's teeth and arch. Although the use of a study model 100A or image 100B is advantageous for manual selection methods, the use of alternative representations may be more advantageous for automated methods. If manual selection methods are to be used, it will generally be desirable that PIAC representation 110 be. visible. However, all that is required of a PIAC representation 110 is that it be comparable to a representation of one or more archwires. As such, the type of representation used will be at least partially dependent on the manner in which comparisons are to be made.

Figure 4:
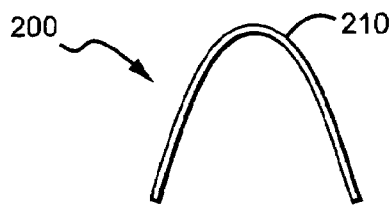
FIG. 4 is a top view of a tapered archwire.

Selecting an archwire shape will generally comprise comparing the PIAC representation 110 to existing archwire shapes and selecting the archwire shape that most closely corresponds to the PIAC 110. It is contemplated that a larger number of patients will have PIAC shapes that correspond to one of three archwire shapes, square, tapered, and ovoid. FIGS. 4–6 depict three archwires 200 having the three shapes, square archwire 210, tapered archwire 220, and ovoid archwire 230. It is contemplated that arch shapes other than those shown in FIGS. 4–6 may be used, but that the three shown provide the best fit to reduce the manufacturing and inventory needed to use preformed shapes and sizes in private practice.

It is preferred that selection of an archwire shape be accomplished by comparing a representation of an available archwire to the PIAC representation 110. The use of an archwire representation for comparison in place of an actual archwire is thought to advantageous, if not actually required, for use in automated archwire selection methods. The use of an archwire representation also provides advantages in manual selection methods as such a representation is generally cheaper than an actual archwire, maintaining the integrity of the representation is generally easier than doing the same for an archwire, and storing the representation is easier than storing the archwire. In less preferred methods, selection of an archwire shape may be accomplished by simply viewing the PIAC representation to determine its shape, the determined shape becoming the selected archwire shape.

Figure 10A:
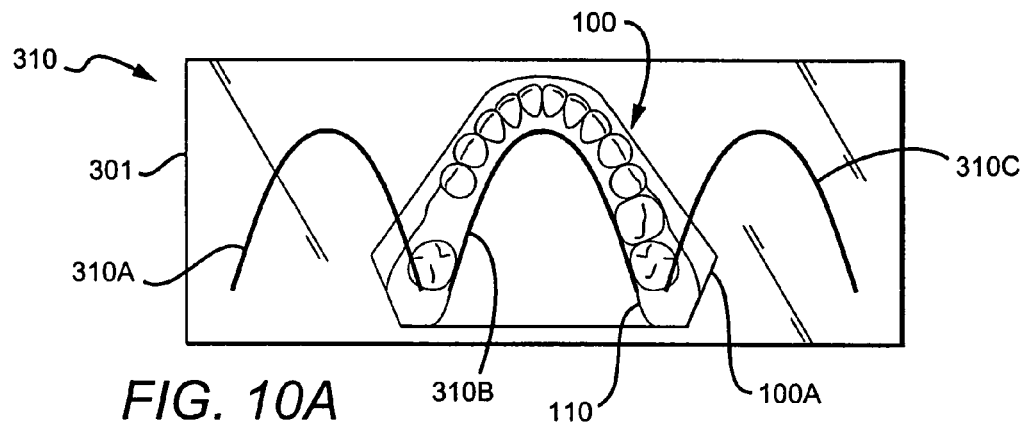
FIG. 10A is a top view of a translucent sheet bearing archwire representations superimposed on a patient's study model to compare the representations to the patient's PIAC.

Referring to FIGS. 7–9, it is contemplated that, particularly for manual methods, providing one or more sets 300 of archwire representations (310A–310C, 320A–320B, 330A–330D) on a transparent or translucent sheet 301 facilitates selection of an archwire shape as the members of the collection can be visually compared to the PIAC by superimposing the individual archwire representations on the PIAC representation as shown in FIG. 10A. A given set may comprise representations of each shape of archwire, representations of different sized archwires of a given shape as was done in FIGS. 7–9, or a combination of different archwire shapes and sizes. A given set may also include variations on sizes that correspond to treatment options such as non-extraction vs. extraction. FIG. 7 shows a set 300 of tapered shaped archwire representations 310A–310C, with 310A being a small tapered archwire, 310B being a medium tapered archwire, and 310C being a non-extraction tapered archwire. FIG. 8 shows a set 300 of square shaped archwire representations 320A–320B, with 320A being a medium square archwire, and 320B being a large square archwire. FIG. 9 shows a set 300 of ovoid shaped archwire representations 320A–320B, with 330A being a small ovoid archwire, 330B being a medium ovoid archwire, 330C being a first non-extraction ovoid archwire, and 330D being a second non-extraction ovoid archwire.

Figure 10B:
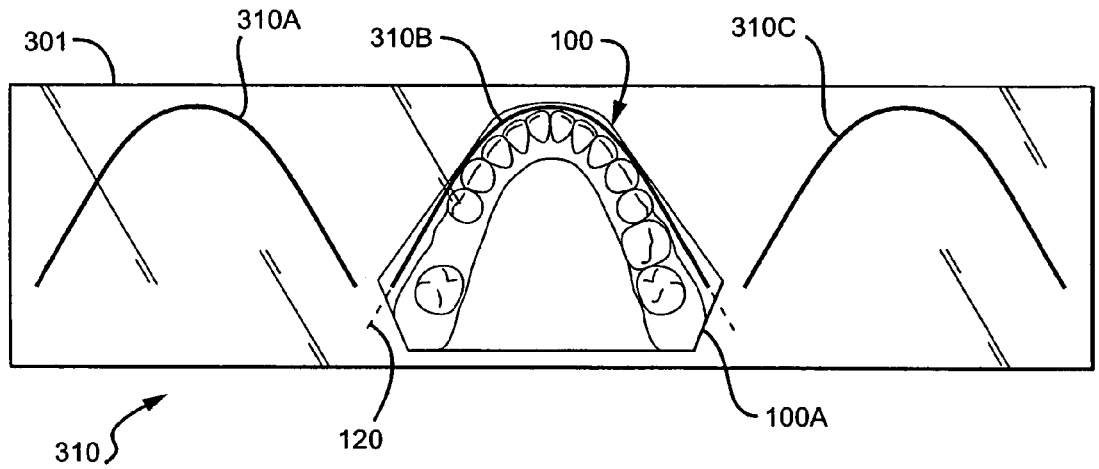
FIG. 10B is a top view of a translucent sheet bearing archwire representations being compared to the curve formed by the labial and buccal surfaces of a patient's teeth.
Figure 11A:
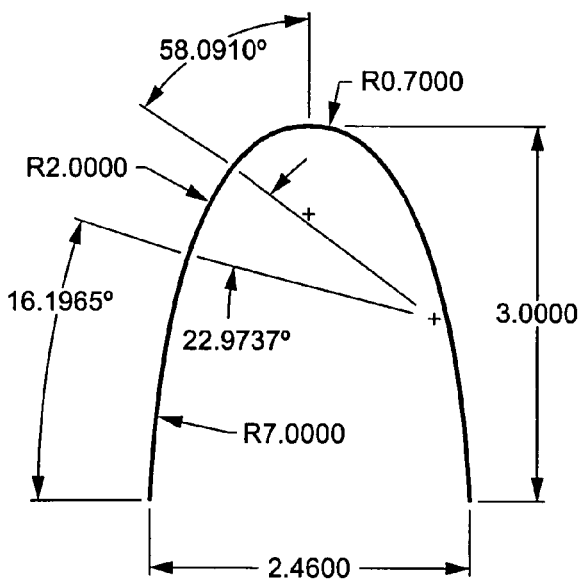
FIG. 11A is a dimensioned view of a small, tapered, lower archwire.
Figure 11B:
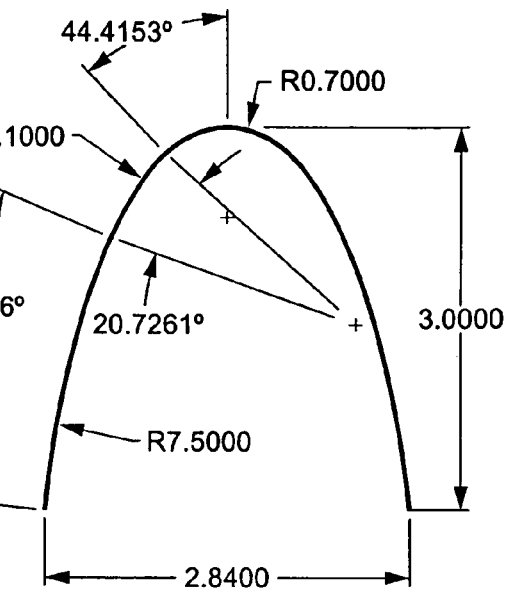
FIG. 11B is a dimensioned view of a medium, tapered, lower archwire.
Figure 11C:
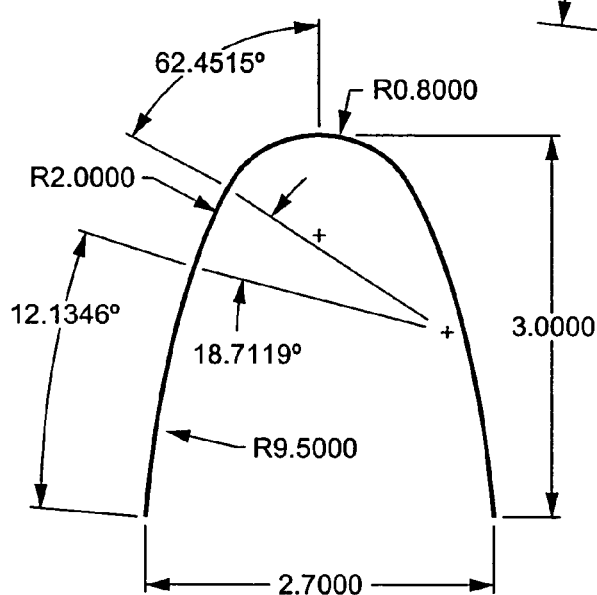
FIG. 11C is a dimensioned view of a non-extraction, tapered, lower archwire.
Figure 11D:
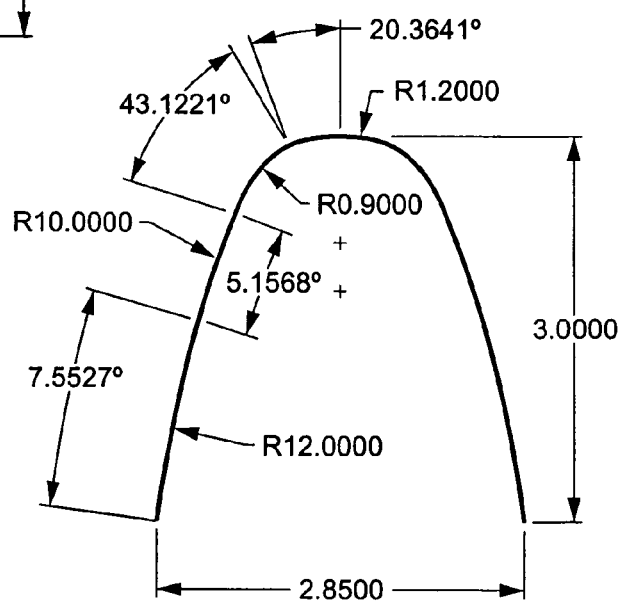
FIG. 11D is a dimensioned view of a medium, square, lower archwire.
Figure 11E:
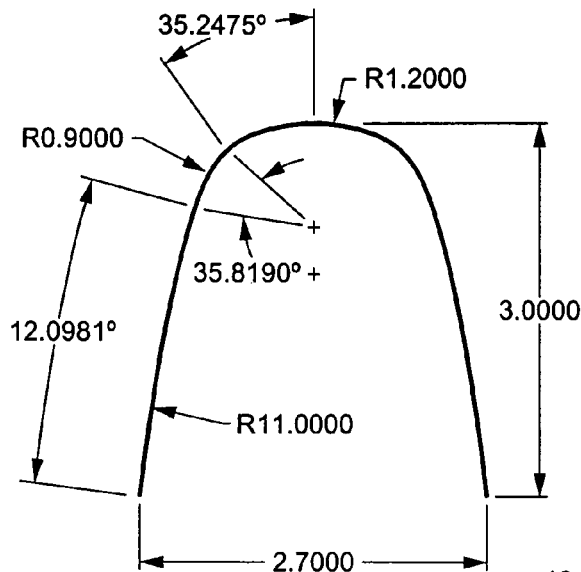
FIG. 11E is a dimensioned view of a large, square, lower archwire.
Figure 11F:
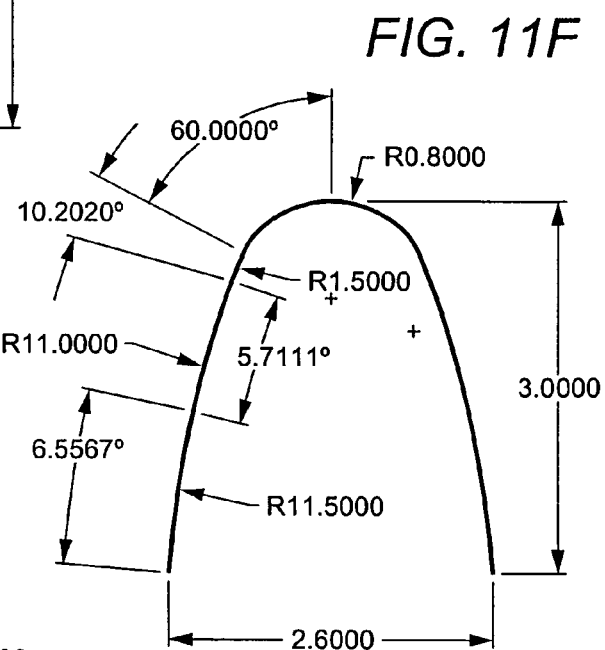
FIG. 11F is a dimensioned view of a small, ovoid, lower archwire.
Figure 11G:
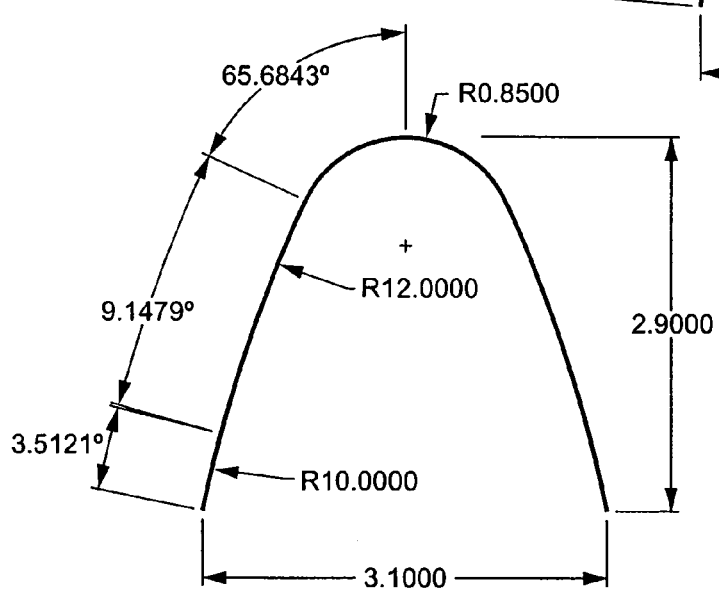
FIG. 11G is a dimensioned view of a medium, ovoid, lower archwire.
Figure 11H:
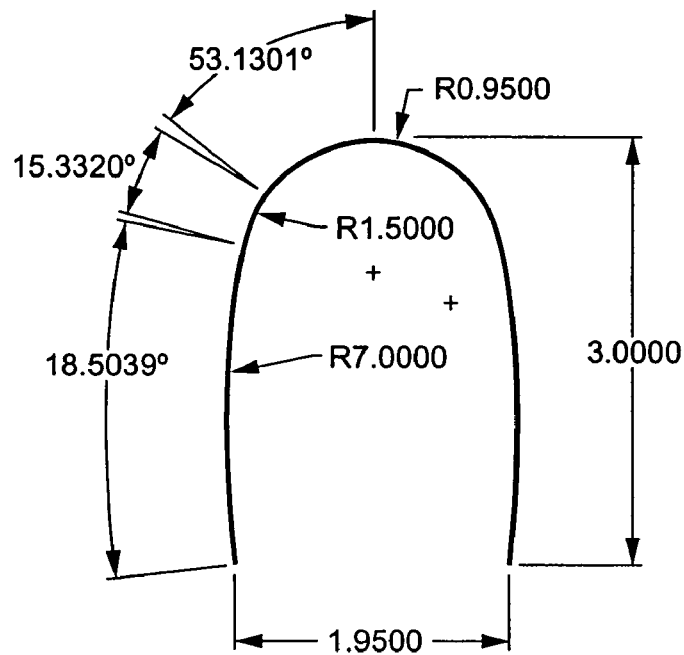
FIG. 11H is a dimensioned view of a first non-extraction, ovoid, lower archwire.
Figure 11I:
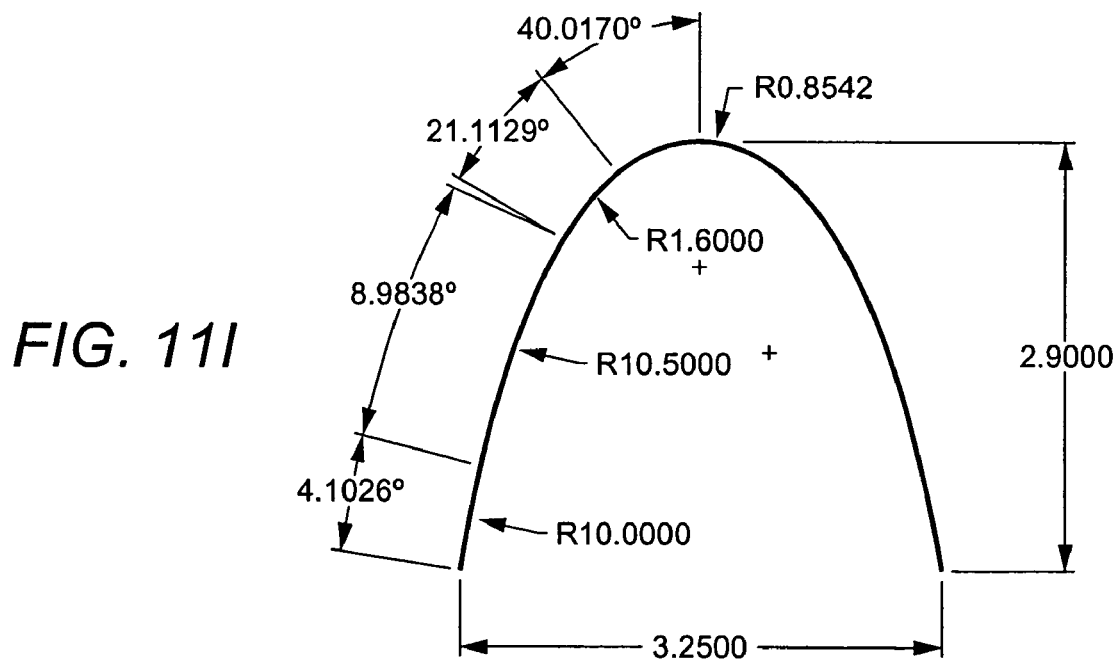
FIG. 11I is a dimensioned view of a second non-extraction, ovoid, lower archwire.
Figure 12A:
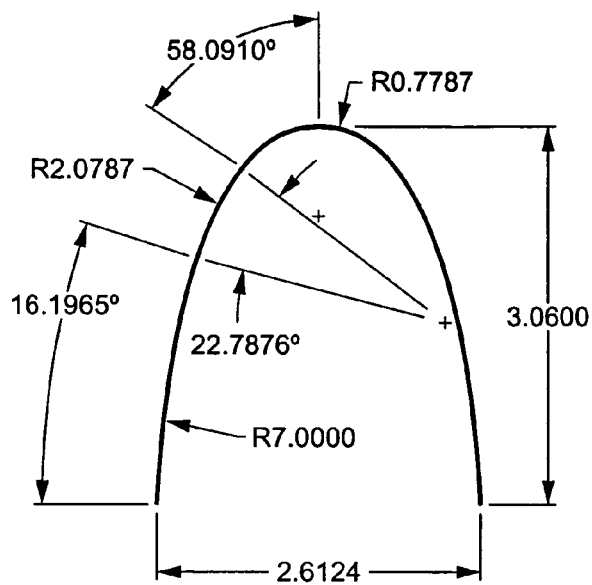
FIG. 12A is a dimensioned view of a small, tapered, upper archwire.
Figure 12B:
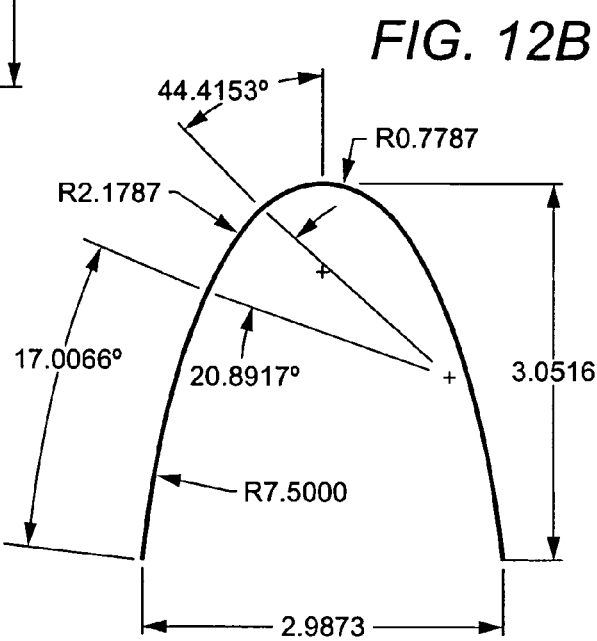
FIG. 12B is a dimensioned view of a medium, tapered, upper archwire.
Figure 12C:
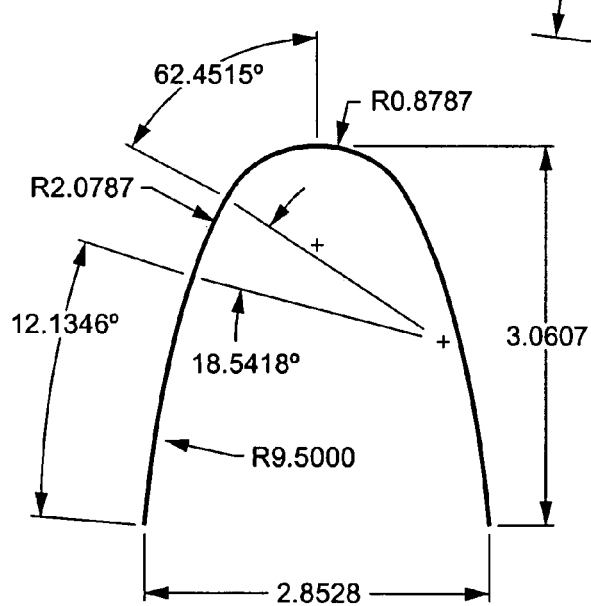
FIG. 12C is a dimensioned view of a non-extraction, tapered, upper archwire.
Figure 12G:
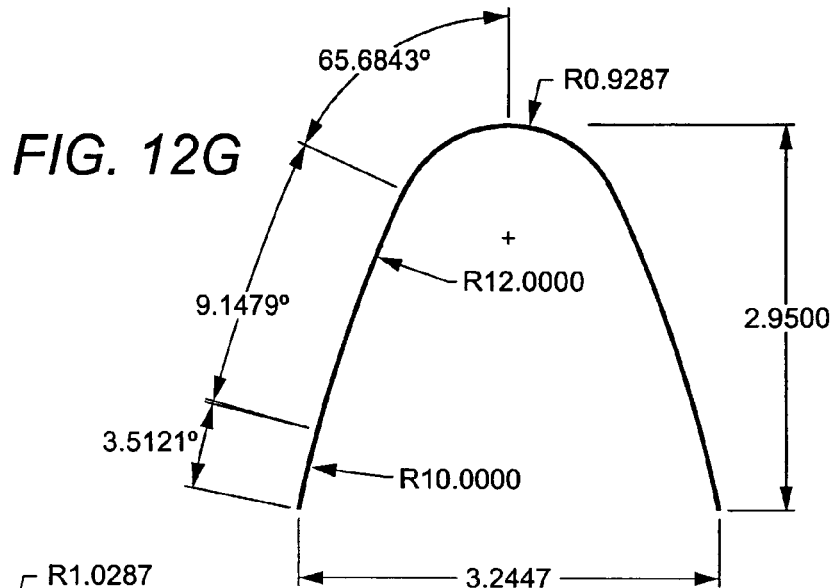
FIG. 12G is a dimensioned view of a medium, ovoid, upper archwire.
Figure 12H:
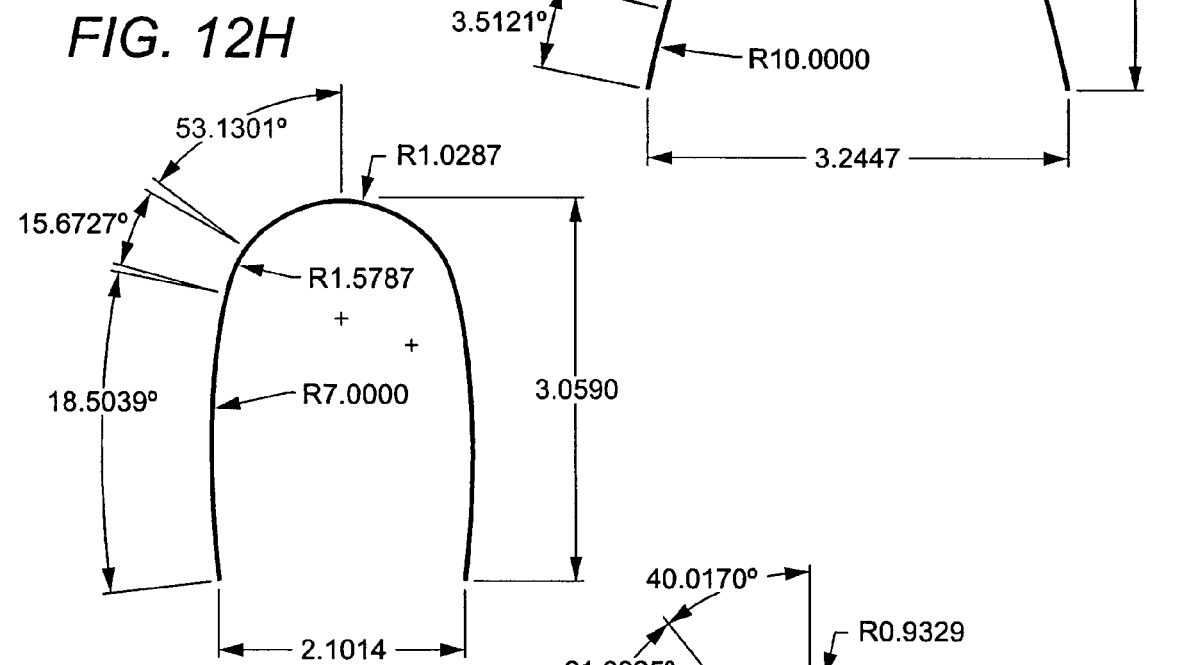
FIG. 12H is a dimensioned view of a first non-extraction, ovoid, upper archwire.
Figure 12I:
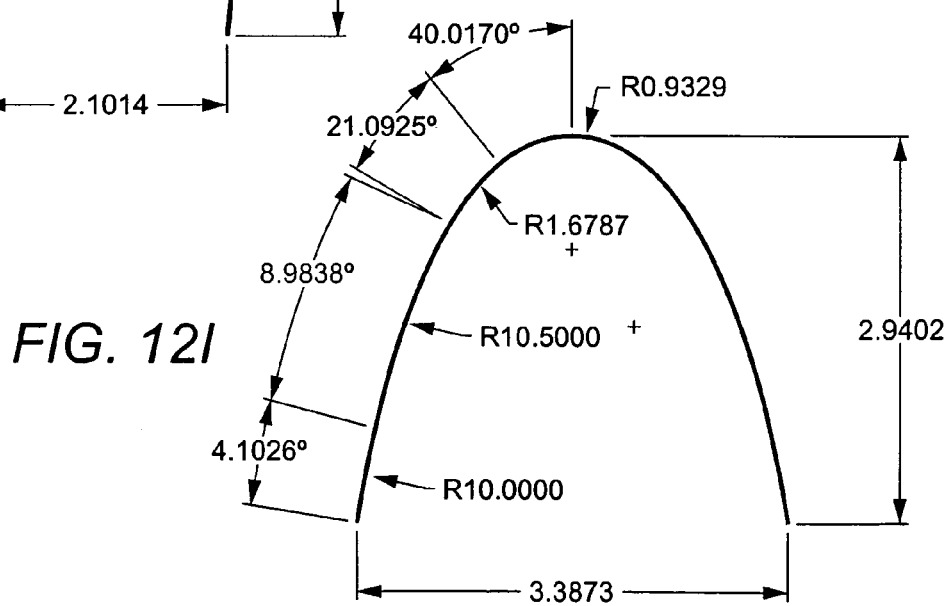
FIG. 12I is a dimensioned view of a second non-extraction, ovoid, upper archwire.

Selecting an archwire size will generally comprise comparing the PIAC 110 to existing archwire sizes (see FIG. 10A) and selecting the archwire size that most closely corresponds to the PIAC 110. This initial selection will often be done simultaneously with the selection of the archwire shape by comparing various archwire representations to the PIAC representation 110. After an initial size selection is made, a final selection will be made based on criteria other than the PIAC 110. Typically this will involve comparing various archwire representations with the curve 120 formed by the outside (labial and buccal) surfaces of a patient's teeth (see FIG. 10B and FIG. 2) and determining which representation best corresponds to that curve. If a particular treatment option is to be chosen, the comparison may be limited to a subset of archwire sizes that correspond to the chosen treatment. Thus, on the same patient, one diagnosis (non-extraction) may require a larger size than the patient's original, naturally determined, arch size. In another treatment choice, the arch shape and size may be maintained, and in others, the shape and size may be constricted.

As an example, study model 100A may be that of a patient who wants the wider smile that a non-extraction treatment could bring. Having obtained study model 100A, a dentist would then pull out one or more transparent sheets 301 bearing representations (310–330) of the archwires (210–230) available to the dentist. The dentist would first determine the appropriate archwire shape to be used by superimposing the different archwire representations on the study model to see which representation best fit the PIAC reproduced by the study model. For the sake of this example, we will assume that a small ovoid archwire best fits the patient's PIAC. Having determined the shape and that the final size will not be smaller than the small ovoid, the next step is to determine which size is appropriate. Since a non-extraction plan is to be followed, the small/first and medium/second non-extraction representations will be superimposed on the study model so that the dentist can visually determine which best fits the curve that will be formed when a wire is mounted to brackets coupled to the patient's teeth.

It is contemplated that the method of archwire selection discussed herein is particularly well adapted for implementation in an automated system 400 for archwire selection. It is contemplated that such a system 400 would beneficially comprise a patient internal arch curve 410 recorder adapted to obtain a representation 415 of a patient's internal arch curve; data 420 on available archwires; and a mechanism 430 adapted to compare an obtained representation 415 of a patient's internal arch curve with the data 420 on available archwires and to identify an archwire based on any such comparison. Such a system 400 would also preferably include means 440 for accepting a treatment diagnosis 450 for the patient.. It is also preferred that either the curve recorder 410 or some other means be used to provide additional data 460 (such as current position, orientation, shape, and size) on the patients teeth. It is also preferred that such a system be integrated into a system 500 that facilitates the ordering of the selected archwire and other orthodontic hardware to minimize or eliminate the need for a dentist/orthodontist to stock archwires. Such a system will generally comprise means 510 for selecting an archwire from a plurality of available archwires, and means 520 for ordering the selected archwire from an archwire supplier. In such a system 500, the selection of an archwire will likely be based, at least in part, on all of the following factors: the patient's jawbone structure; a dentists preferred treatment option; and the sizes and shapes of available archwires.

A patient internal arch curve recorder 410 adapted to obtain a representation of a patient's internal arch curve 415 may comprise a modern imaging system capable of providing the required electronic representation directly. Alternatively, such a recorder 410- may simply comprise a scanner or digital camera which digitizes a representation (such as a study model or physical image) obtained through other means. Similar methods may be used to obtain additional data 460 on the current state of the patient's teeth such as current position, orientation, shape, and size.

The data 420 on available archwires is preferably a database of available archwires with sufficient data on each available archwire to permit comparison, primarily in regard to shape, with the patient's PIAC, the curve formed by the outside (labial and buccal) surfaces of the patients teeth, and the desired treatment option. In some instances, such data 420 may be provided in electronic form directly from one or more archwire manufacturers. In other instances, such data may be obtained directly from examination of actual archwires.

A mechanism 430 adapted to compare an obtained representation of a patient's internal arch curve 415 with the data 420 on available archwires may use one or more known comparison methods adapted for comparing curves and/or data sets. It is contemplated that such a mechanism 430 may operate to identify an ideal curve based on the patients PIAC, the current state of the patient's teeth, the desired treatment option, and the next step to be performed in following that treatment option. Once such an idealized curve is identified, it may be compared to the data available on available archwires to select an available archwire best adapted to accomplish the next step of the treatment. Alternatively, such a mechanism 430 may simply plug all the data available on the patient and the available archwires into a complex algorithm that will identify the archwire to be used. Regardless of the method used, the results of the comparison need to be communicated to the dentist/orthodontist. It is preferred that the results be communicated directly to the dentist. The results may be communicated indirectly if the system is integrated with an ordering system such that the dentist is notified by receipt of an archwire, but such a system may be less than desirable if possible errors in treatment are to be minimized.

Any means 440 for accepting a treatment diagnosis 450 for the patient that facilitates the use of the diagnosis in selecting an archwire may be used. Such means 440 will typically include the use of a keyboard and monitor to accept input and provide verification of correct input to the dentist. Alternatively, other means may be used such as systems designed to accept voice input and to provide audio confirmation and/or output.

Integration into a system 500 that facilitates the ordering of the selected archwire and other orthodontic hardware is preferred in order to minimize or eliminate the need for a dentist/orthodontist to stock archwires. Ideally, the dentist/orthodontist would need to supply only a treatment diagnosis to the system, and facilitate the system's obtaining data on the patients teeth and jaw bone structure, confirm that an archwire or set of archwires is to be ordered, and then wait for delivery of the ordered archwire(s). Although stocking of some archwires may facilitate a just-in-time system of inventory in which inventory is replaced as used, it is preferred that little or no inventory of archwires be maintained and that archwires be obtained on an as-needed basis. Although there will generally be a delay between the determination of the archwire to be used and the dentists receipt of the archwire and/or use of it on the patient, such a delay is considered to be acceptable in light of the savings to be achieved by reducing or eliminating the dentist's inventory of archwires. Such a saving becomes even more significant as the number of shapes, sizes, and types of available archwires increases. Reference to FIGS. 11A–11I and 12A–12I provide an indication of the impact of such an increase when one considers that in many instances a single archwire shape and size may have been previously used and stocked in place of the archwires shown.

Although the system and method discussed are generally applicable regardless of the archwire shapes and sizes available, it is contemplated that having the archwires shown in FIGS. 11A–11I and 12A–12I may be advantageous. The pictured set of archwires is contemplated to be a set of archwires that embodies a desirable balance of the advantages and disadvantages relating to the number, size, and shape of archwires available.

Thus, specific embodiments and applications of archwire selection systems and methods have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An automated system for selecting an archwire for a patient comprising:
    a patient internal arch curve recorder adapted to obtain a representation of the patient's internal arch curve;
    data on available archwires;
    a machine readable medium containing instructions which, when executed by a machine, cause the machine to compare an obtained representation of a patient's internal arch curve with the data on available archwires and to identify an archwire based on any such comparison.

2. The system of claim 1 wherein the system further comprises data relating to the current position, orientation, shape and/or size of the patient's teeth.

3. The system of claim 1 wherein the system further comprises an input mechanism adapted to accept a treatment diagnosis.

4. The system of claim 3 wherein the instructions also cause the machine to utilize an input treatment diagnosis in identifying an archwire.

5. The system of claim 1 wherein the system comprises a communications mechanism adapted to communicate to an archwire supplier that the identified archwire is to be provided to a user of the system.

6. The system of claim 1 wherein the patient internal arch curve recorder comprises a means for obtaining an electronic representation of at least a portion of a study model or image.

7. The system of claim 6 wherein the patient internal arch curve recorder comprises a digital camera or scanner.

8. The system of claim 1 wherein the data on available archwires comprises data on archwires comprising one of at least three different shapes.

9. The system of claim 8 wherein the data on available archwires comprises data on at least two archwires having the same shape wherein one of the archwires is adapted for use in a non-extraction treatment plan and another of the archwires is adapted for use in an extraction treatment plan.

10. The system of claim 1 wherein the instructions cause the machine to identify an archwire based on the shape of the patient's internal arch curve.

11. The system of claim 10 wherein the instructions cause the machine to identify an archwire by comparing the shape of the patient's internal arch curve with the shapes of available archwires.

12. An automated system that includes a machine readable medium having one or more instructions for selecting an archwire for a patient which when executed by a processor cause the processor to select an archwire by:
    obtaining a representation of the patient's internal arch curve (PIAC);
    selecting an archwire shape based at least partially on the PIAC representation; and
    selecting an archwire to be used based on the selected archwire shape.

* * * * *